United States Patent [19]  [11] 4,173,416
Pugsley et al.  [45] Nov. 6, 1979

[54] SCANNING HEADS FOR TRANSPARENCIES

[75] Inventors: Peter C. Pugsley, Pinner; Michael J. Perriman, Harpenden, both of England

[73] Assignee: Crosfield Electronics Limited, London, England

[21] Appl. No.: 808,799

[22] Filed: Jun. 22, 1977

[30] Foreign Application Priority Data

Jun. 26, 1976 [GB] United Kingdom ............... 26698/76

[51] Int. Cl.² ........................................... G01N 21/06
[52] U.S. Cl. .................................... 356/432; 250/252
[58] Field of Search ................ 250/252, 207 C, 214 P; 356/201, 213, 202, 209, 203, 219, 175, 176; 355/38, 32, 68, 83, 81; 73/26

[56] References Cited

U.S. PATENT DOCUMENTS

| 3,244,062 | 4/1966 | Sweet | 356/203 |
| 3,406,290 | 10/1968 | Brueschke | 356/203 |
| 3,711,209 | 1/1973 | Caspersson et al. | 356/203 |
| 4,025,189 | 5/1977 | Pugsley | 355/38 |
| 4,061,428 | 12/1977 | Amano et al. | 356/175 |

Primary Examiner—John K. Corbin
Assistant Examiner—B. W. de los Reyes
Attorney, Agent, or Firm—Weingarten, Maxham & Schurgin

[57] ABSTRACT

For presetting values of parameters in an image-reproducing process, an operator selects a spot on a transparency to be reproduced, for example by visual inspection of a projected image of an area of the transparency illuminated by a defocused light beam. The light beam is then temporarily brought to a focus on the selected spot and the light transmitted through the transparency on a photomultiplier, the signal from which is sampled within a very short period and held, after which the focused light beam is again defocused to enable the operator to select a further spot. The value of the sample signal is used in the presetting of the said parameter values. The period for which the focused light beam falls on the transparency is made small enough to avoid the bleaching of the transparency at the illuminated spot.

5 Claims, 5 Drawing Figures

SCANNING HEADS FOR TRANSPARENCIES

A peculiar property of some transparency materials is their susceptibility to temporary bleaching under intense illumination. This bleaching occurs in a period of 1-2 seconds and results in a reduction of density of the order of 0.2 or 0.3 density units. The phenomenon is reversible, that is to say when the illumination is removed, the original density is restored. Of course if the illumination is too intense, or is maintained for too long a period, permanent damage is produced.

This temporary bleaching phenomenon can cause a good deal of trouble when setting up a scanner to scan a transparency, since the setting adjustments are usually made with the transparency stationary in the illuminating spot. The adjustments are thus made on the bleached state of the transparency, whereas when scanning commences, the transparency is moving rapidly through the illuminating spot and there is therefore no time for the temporary bleaching to occur. The problem does not arise with all transparency materials, but it is particularly likely to occur with materials which have been poorly processed. It is therefore difficult to detect when the phenomenon has occurred and there is therefore a clear requirement for a scanner in which the setting up adjustments will be unaffected by occurrence of this phenomenon.

Thus, the present invention is concerned with a scanning image analyser comprising a transparency support and a photo-electric image analyser mounted for relative movement either for continuous scanning of an image-bearing transparency placed on the support or under the control of an operator, the image analyser comprising means for focusing light from a light source to a spot on the transparency and photo-electric means receiving light from the source which has passed through the transparency, whereby during the said continuous scanning movement an image-representing signal is obtained from the photo-electric means; according to the invention, the analyser also comprises, for use in a preliminary parameter-setting operation, measuring means including means for temporarily illuminating with a focused light beam a spot on the transparency selected by the operator and means operable within a predetermined period following the initiation of the temporary illumination of the selected spot to sample and hold the value of the signal derived from the photo-electric means for recording, indicating or processing, the said period being insufficient for the light spot to cause bleaching of the transparency. In the preferred form of apparatus embodying the invention, the analyser comprises a viewing means which includes defocusing means for spreading the light from the source over a selected area of the transparency and means for presenting an image of the illuminated area for viewing by an operator. This enables the operator to select the spot the density of which is required to be measured. Thus, in such an apparatus prior to a scanning operation the defocusing means is effective and the operator views an image of an illuminated area. For measuring the density of a selected spot, the light spot is focused, the selected spot is temporarily illuminated and the sample and hold circuit derives its signal from the phot-electric means; and for subsequent scanning the beam is focused and is effective throughout the scanning operation to cause the photo-electric means to generate a signal which is continuous or substantially continuous and represents the image densities of the successively scanned points of the image.

In this way, the density of the selected spot is measured without the spot having been bleached before the measuring takes place.

In one embodiment of the invention, an auxiliary lens is inserted in the light beam to defocus the light spot for normal viewing of the transparency before taking a density measurement, and the movement of the auxiliary lens out of the light beam is timed to occur just before the sample-and-hold circuit is triggered, the sample-and-hold circuit being arranged to sample the value of the signal from a photomultiplier which receives the light transmitted through the transparency. The sample-and-hold circuit may comprise, for example, an analogue-to-digital converter responsive to the output from the photomultiplier, a conversion cycle of the converter being triggered each time a sample-and-hold is desired. The digital output is then maintained indefinitely for subsequent processing and display of the numerical value.

In one alternative embodiment of the invention, the transparency is only momentarily illuminated with the focused light spot and the measurement of the amount of light transmitted through the transparency is synchronised to take place at the same time as the transparency is illuminated. In this case a number of measurements are normally made at the same spot on the transparency and the measurements are averaged.

In order that the invention may be better understood, two forms of apparatus embodying the invention will now be described with reference to the accompanying drawings, in which.

Figure 1:
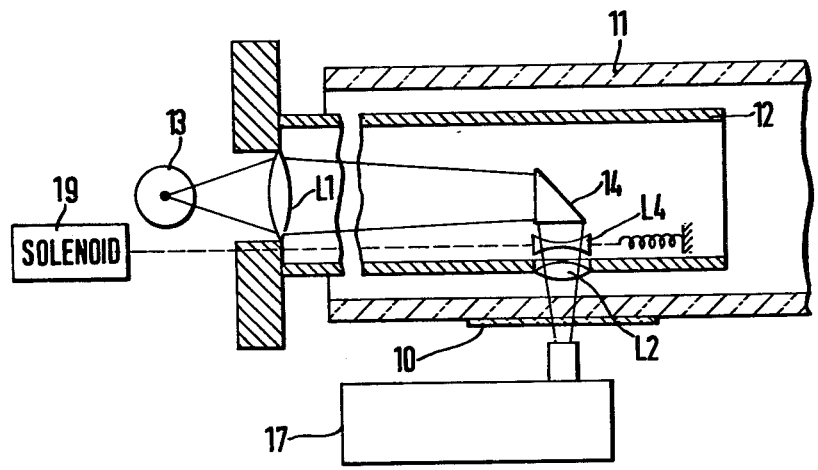
FIG. 1 is a schematic sectional view of an analysing scanner and the associated measuring circuits.
Figure 2:
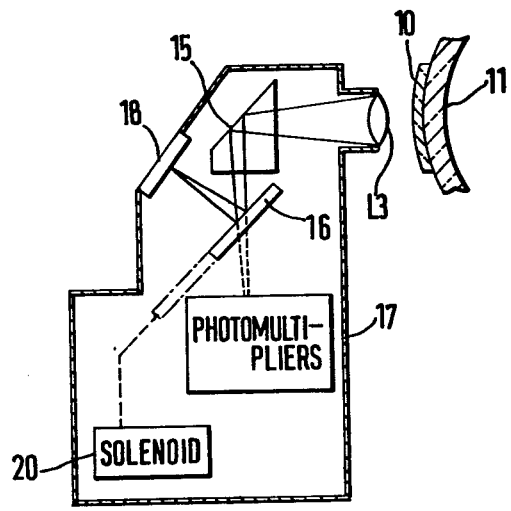
FIG. 2 is a schematic view of the analysing scanner in the direction of the arrow A shown in FIG. 1.

In FIGS. 1 and 2, a transparency 10 is mounted on the periphery of a transparency drum 11. The diagram shows only the essential optical parts of the scanner which are located in a tube 12 positioned within the drum 11. Light from a xenon lamp 13 enters the tube at one end and is directed by a lens L1 on to a prism 14 which deflects the light downwards through a lens L2 in the wall of the tube 12 and thence through the transparency drum 11 and the transparency 10.

The light emerging from the transparency drum is received by an objective lens L3 (FIG. 2) and is then redirected by a prism 15 eighter on to a sliding mirror 16 (when the mirror is in the position shown in FIG. 2) or into the scanning head 17 (when the mirror is moved to the position shown in dashed outline in FIG. 2). The scanning head is of a conventional type and will normally include apertures, colour filters and photomultipliers for recording the strength of the signal received from the transparency. In practice, sharp and unsharp apertures, beam-splitters, dichroic filters and four photomultipliers might be included within the head.

When the sliding mirror 16 is in the position shown in FIG. 2, the light beam is directed on to a translucent viewing screen 18 so that the illuminated portion of the transparency can be viewed before taking any measurement. When viewing the transparency in this manner, the illuminating light spot is defocused, and this is achieved by inserting into the light beam an auxiliary lens L4 (FIG. 1). This normally rests in the light path but during scanning of the transparency or during the taking of a setting-up measurement, a solenoid 19 is energised to pull the lens L4 out of the light beam. A focused light spot then falls upon the transparency. The intensity of the defocused light spot is much less than that of the focused light spot and it is therefore only when the focused light spot is incident on the transparency that the temporary bleaching phenomenon may occur.

The sliding mirror 16 shown in FIG. 2 is moved between the two positions shown in response to the energisation and de-energisation of a solenoid 20. This solenoid may be, for example, a rotary solenoid and may act on the mirror through a rack and pinion.

Figure 3:
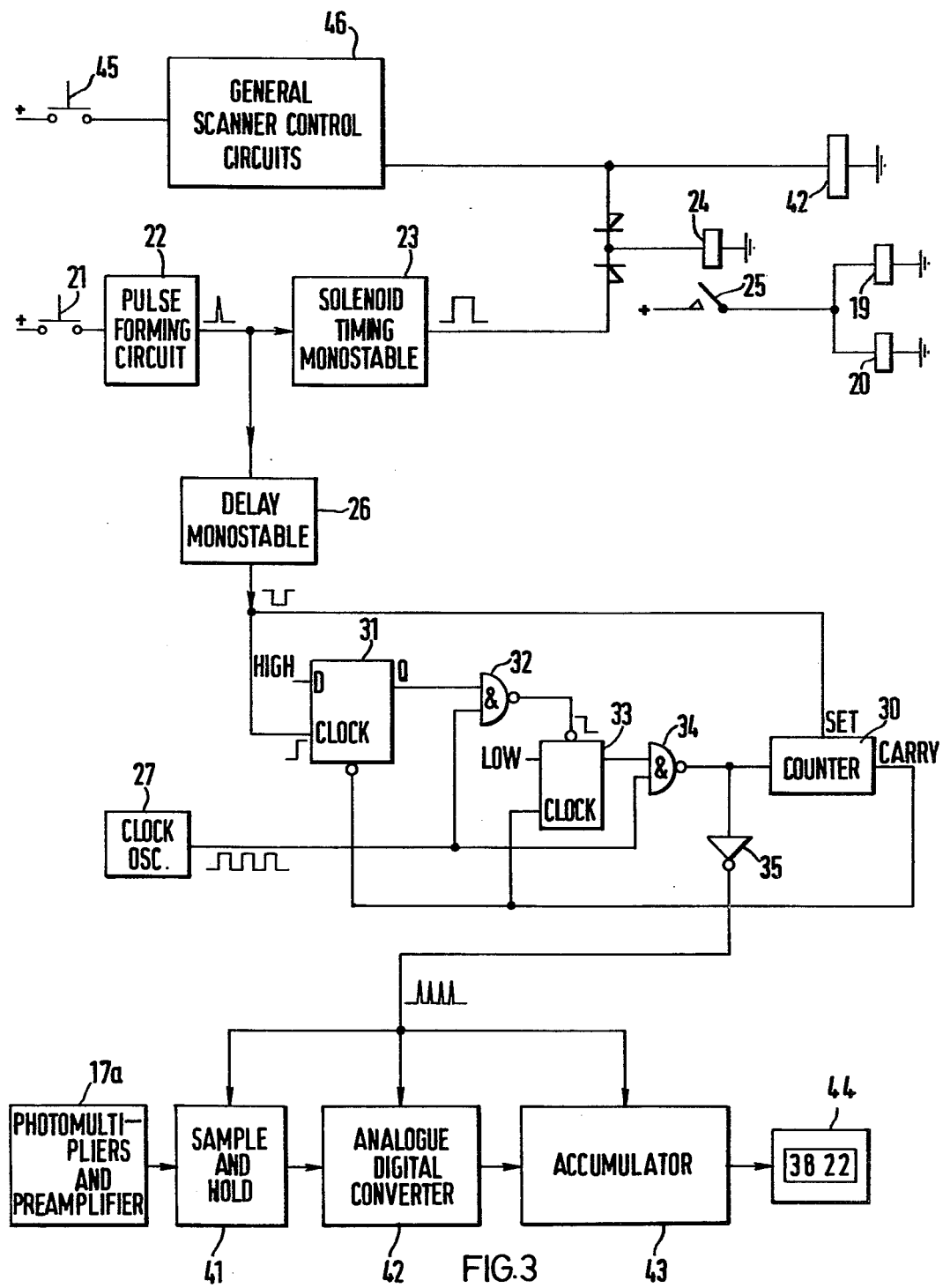
FIG. 3 is a block diagram of the circuit, including sequence control, for the apparatus shown in FIGS. 1 and 2.
Figure 4:
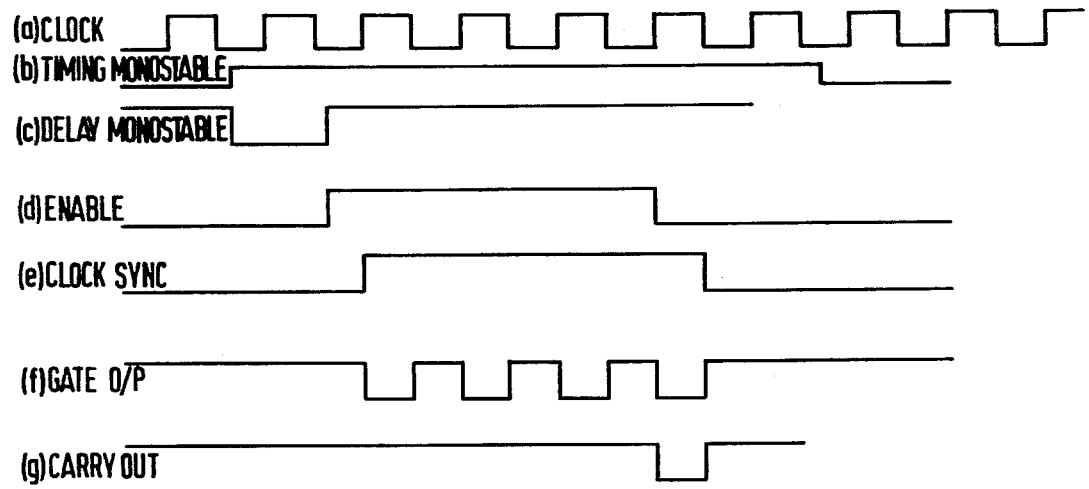
FIG. 4 is a timing diagram for the circuit of FIG. 3.

The operating sequence of the scanner shown in FIGS. 1 and 2 will now be described with reference to these Figures and to FIG. 3, which shows a block circuit diagram illustrating the sequence control, and FIG. 4 which is a timing diagram for parts shown in FIG. 3.

In the normal rest state of the scanner, the auxiliary lens L4 is in the light path and the sliding mirror 16 is in the position shown in full lines in FIG. 2 where it reflects an image of a selected area of the transparency on to the viewing screen 18. The transparency drum 11 can then be moved as required to select a desired area of the transparency for observation on the viewing screen 18 by an operator. The transparency is not susceptible to bleaching at this stage because the light spot illuminating the selected area is defocused.

When the operator wishes to make a measurement of the light transmitted through a selected spot on the transparency to permit him to make preliminary adjustments to the settings of the analyser prior to the scanning operation, he aligns the selected spot with the known position of the light beam when focused. He then operates a switch 21 which acts through a pulse forming circuit 22 to initiate the operation of the solenoid timing monostable circuit 23. The circuit 23 energises the coil 24 of a solenoid relay, the contact 25 of which completes a circuit for the auxiliary lens solenoid 19 and the mirror solenoid 20. The energisation of these two solenoids results in movement of the auxiliary lens L4 and the mirror 16 out of the light path, so that a focused light beam now passes through the selected spot of the transparency to a photomultiplier or photomultipliers in the scanning head 17.

Simultaneously with the application of the pulse from the circuit 22 to the solenoid timing monostable circuit 23, a pulse is applied to a delay monostable 26. As is evident from the waveforms b and c shown in FIG. 4, the delay monostable 26 generates a pulse which is much shorter than that generated by the circuit 23, the purpose of the pulse from the delay monostable 26 being to ensure that application of pulses from a clock oscillator 27 (waveform a) to a pulse counter is delayed until the solenoids 19 and 20 have completed the operations of moving the auxiliary lens 14 and mirror 16. The manner in which the pulses reach the counter will now be described. The trailing positive-going edge of a pulse on the delay monostable 26 sets a counter 30 to zero and is also applied to the "clock" input of a first D-type flip-flop 31, which will be referred to as the enabling flip-flop. As the D input of this flip-flop is permanently wired to a high voltage level, the pulse from the circuit 26 results in a high level at the Q output of flip-flop 31 and therefore at one input of an AND gate 32. As a consequence, the next pulse from the clock oscillator 27 passes through the AND gate 32 to the preset terminal of a second D-type flip-flop 33, which will be known as the clock sync flip-flop. The D input of the flip-flop 33 is permanently wired to a low voltage level. The inverted output of the AND gate 32 results in a signal from the flip-flop 33 which enables a further AND gate 34 to pass inverted clock pulses from the oscillator 27 to the counter 30. Waveform e in FIG. 4 shows the output of the clock sync flip-flop and waveform f is the output of gate 34. When the fourth clock pulse reaches the counter, the counter generates a "carry" pulse at its output (waveform g, FIG. 4) and this is applied to the clock input of the flip-flop 33 and the preset terminal of the flip-flop 31. The leading negative-going edge of this "carry" pulse reverses the output of the flip-flop 31 and the trailing positive-going edge of the carry pulse reverses the output of the flip-flop 33. This blocks the gate 34 so that it passes no further clock pulses.

The four pulses which are passed by the gate 34 are also applied through an inverter amplifier 35 to a sample-and-hold circuit 41 which at each clock pulse samples the output of the photomultiplier and preamplifier circuit 17a and holds this value while an analogue-digital converter 42, also triggered by the clock pulse from amplifier 35, converts the held value to digital form and applies its digital output to a data processing circuit 43. The circuit 43 includes an averaging means to take the average of the 4 digital outputs from the converter 32, corresponding to the 4 samples taken in response to the clock pulse circuits. The averaging means may for example comprise an accumulator the output of which is effectively displaced two places to the right to effect the division by 4. The digital output of the circuit 43, representing the average of the 4 readings, is applied to a digital display device 44.

The pulse from the timing monostable 23 is long enough to ensure that the four readings have been taken. At the end of this pulse the solenoids 19 and 20 release and the apparatus returns to its viewing condition.

The solenoids 19 and 20 are also energised by the relay 24 when a switch 45 is actuated to start a scanning operation. This closes a circuit to the general scanner control circuits 46 which energise the relay 24 and a relay 42 controlling the energisation of the motor for producing relative movement of the drum and scanning head.

Figure 5:
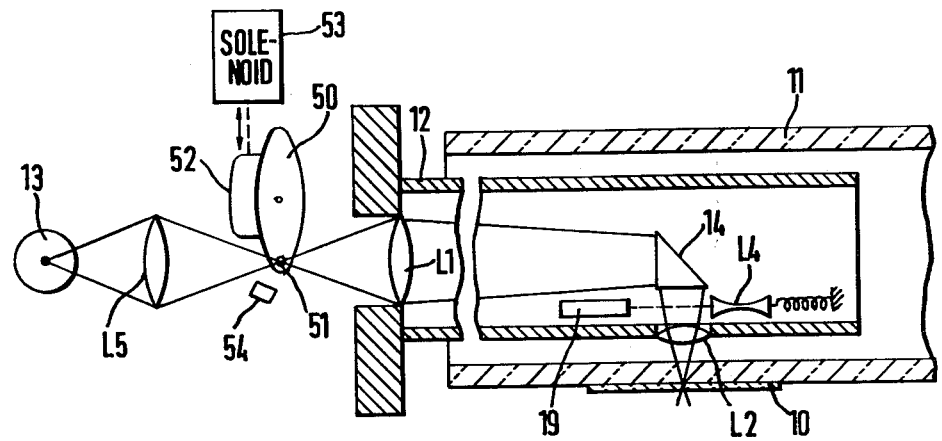
FIG. 5 illustrates diagrammatically a second form of analysing scanner embodying the invention.

FIG. 5 shows the arrangement of the beam generating means and transparency drum in an alternative form of the invention in which a rotating chopper disc 50 is formed with a small hole 51 and interrupts the passage of light from the source 13 to the tube 12 for about 99% of the time required for the disc to complete a revolution. An additional lens L5 focuses light from the source at the disc 50. The disc 50 is rotated by a small motor 52 and the assembly of motor and disc is mounted on a rocking or rotating frame operated by a solenoid 53 so that the disc can be completely withdrawn from the light path when not required. In an alternative form, an electromagnet is energised to attract a small armature attached to the disc so that the disc is held stationary in a position in which light passes through the hole 51 during viewing or scanning operations.

A photocell 54 receives light reflected from the incident side of the disc 50 and generates a trigger signal whenever the passage of the hole 51 through the light beam interrupts the reflected light received by the photocell 54. The output of the photocell 54 triggers the sample-and-hold circuit. As before, the auxiliary lens L4 is out of the light path during measurements and during scanning. Thus, when measurements are taken focused light reaches the transparency for only 1% of the time and its average intensity is insufficient to cause temporary bleaching.

We claim:

1. Apparatus for image scanning and analysis comprising a transparency support and a photoelectric image analyzer mounted for relative movement either for continuous scanning of an image bearing transparency placed on the support or discontinuously under the control of an operator, the image analyzer comprising a light source, means for directing light from the source to a spot on the transparency, and photoelectric means for receiving light from the source which is passed through the transparency and generating a signal corresponding thereto, wherein the improvement comprises means, for use in a parameter-setting operation preliminary to scanning, comprising:

means under the control of an operator for relatively moving the image analyzer and the transparency support to select for analysis a spot on the transparency; and measuring means including:

means for illuminating the spot on the transparency selected by the operator with a focused light beam for a predetermined period insufficient for the focused light beam to cause bleaching of the transparency; and sampling means operable to sample and hold the value of the signal derived from the photoelectric means during said predetermined period of illumination of said spot with a focused beam.

2. Apparatus in accordance with claim 1, further comprising viewing means including defocusing means for spreading the light from said source over a selected area of the transparency and means for presenting an image of the illuminated area for viewing by the operator; and in which the means for illuminating the selected spot with a focused light beam for a predetermined period insufficient to cause bleaching comprises means operable to temporarily move the defocusing means out of the light path.

3. Apparatus in accordance with claim 2, in which the means for presenting an image of the illuminated area for viewing by an operator includes a mirror movable into and out of the optical path of light which is passed through the transparency and a viewing screen, the measuring means comprising means operable simultaneously to move said mirror and the focusing means out of the path of the light beam.

4. Apparatus in accordance with claim 1, in which the means for sampling the value of said signal operates to sample the signal value a plurality of times in each operation of the measuring means, and said measuring means further includes an averaging circuit for generating an output representing the average of the samples.

5. Apparatus in accordance with claim 1, in which the means for illuminating the selected spot for a predetermined period insufficient to cause bleaching includes a rotating disc and means for moving the rotating disc into the path of light between the light source and the transparency during a measurement, the rotating disc blocking light from the transparency for the major part of rotation, whereby the average illumination of the transparency during measurement is insufficient to cause bleaching.

* * * * *